US008637465B2

(12) United States Patent
Berezin et al.

(10) Patent No.: US 8,637,465 B2
(45) Date of Patent: Jan. 28, 2014

(54) FIBROBLAST GROWTH FACTOR RECEPTOR-DERIVED PEPTIDES BINDING TO NCAM

(75) Inventors: Vladimir Berezin, Copenhagen N (DK); Elisabeth Bock, Charlottenlund (DK); Artur Kochoyan, Brønshøj (DK)

(73) Assignee: Kobenhavns Universitet, Copenhagen K (DK)

( * ) Notice: Subject to any disclaimer, the term of this patent is extended or adjusted under 35 U.S.C. 154(b) by 0 days.

(21) Appl. No.: 13/322,307

(22) PCT Filed: May 27, 2009

(86) PCT No.: PCT/DK2009/050119
§ 371 (c)(1),
(2), (4) Date: Feb. 9, 2012

(87) PCT Pub. No.: WO2010/136031
PCT Pub. Date: Dec. 2, 2010

(65) Prior Publication Data
US 2012/0141451 A1 Jun. 7, 2012

(51) Int. Cl.
*A61K 38/17* (2006.01)

(52) U.S. Cl.
USPC .......... 514/19.1; 514/1.1; 514/17.7; 514/17.8; 514/17.9; 514/21.7; 514/21.6; 530/328; 530/329

(58) Field of Classification Search
None
See application file for complete search history.

(56) References Cited

FOREIGN PATENT DOCUMENTS

WO WO 2007/045247 4/2007

OTHER PUBLICATIONS

Kiselyov, Vladislav V. et al; "Structural basis for a direct interaction between FGFR1 and NCAM and eficence for a regulatory role of ATP." Structure (2003) 11(6) p. 691-701.*
Soroka, Vladislav et al; "Induction of neuronal differentiation by a peptide corresponding to the homophilic binding site of the second ig module of the neural cell adhesion molecule." J. Bio. Chem. (2002) 277(27) p. 24676-24683.*
Knobloch, Marlen and Mansuy, Isabelle M.; "Dendritic spine loss and synaptic alteations in alzheimer's disease." Mol. Neurobiol. (2008) 37 p. 73-82.*
Kitov, Pavel I. and Bundle, David R.; "On the nature of the multivalency effect: a thermodynamic model." J. Am. Chem. Soc. (2003) 125 p. 16271-16284.*
Atkins et al. "Association between the first two immunoglobulin-like domains of the neural cell adhesion molecule N-CAM". FEBS Letters 451 (1999) 162-168.
Berezin et al. "The neural cell adhesion molecule". Current Opinion in Drug Discovery & Development 2000 3(5):605-609.
Brusés and Rutishauser. "Roles, regulation, and mechanism of polysialic acid function during neural development". Biochimie 83 (2001) 635-643.
Cremer et al. "NCAM Is Essential for Axonal Growth and Fasciculation in the Hippocampus". Molecular and Cellular Neuroscience 8 (1997) 323-335.
Delaglio et al. "NMRPipe: A multidimensional spectral processing system based on UNIX pipes". Journal of Biomolecular NMR 6 (1995) 277-293.

Doherty and Walsh. "CAM-FGF receptor interactions: a model for axonal growth". Molecular and Cellular Neuroscience 8 (1996) 99-111.
Itoh and Ornitz. "Evolution of the Fgf and Fgfr gene families". Trends in Genetics vol. 20 No. 11 (2004) 563-569.
Jensen et al. "Structure and interactions of NCAM modules 1 and 2, basic elements in neural cell adhesion". Nature Structural Biology vol. 6 No. 5 (1999) 486-493.
Kasper et al. "Structural basis of cell—cell adhesion by NCAM". Nature Structural Biology vol. 7 No. 5 (2000) 389-393.
Kiselyov et al. "Elucidation of the mechanism of the regulatory function of the Ig1 module of the fibroblast growth factor receptor 1". Protein Sci. 15 (2006) 2318-2322.
Kiselyov et al. "NMR structure of the first Ig module of mouse FGFR1". Protein Sci. 15 (2006) 1512-1515.
Kiselyov et al. "Structural Basis for a Direct Interaction between FGFR1 and NCAM and Evidence for a Regulatory Role of ATP". Structure, vol. 11 (2003) 691-701.
Kiselyov et al. "Structural biology of NCAM homophilic binding and activation of FGFR". Journal of Neurochemistry 94 (2005) 1169-1179.
Kiselyov et al. "The First Immunoglobulin-like Neural Cell Adhesion Molecule (NCAM) Domain Is Involved in Double-reciprocal Interaction with the Second Immunoglobulin-like NCAM Domain and in Heparin Binding". The Journal of Biological Chemistry vol. 272, No. 15 (1997) pp. 10125-10134, 1997.
Kjær et al. "Automated and semiautomated analysis of homo- and heteronuclear multidimensional nuclear magnetic resonance spectra of proteins: The program pronto". Meth. Enzymol. 239 (1994) 288-307.
Kochoyan, A. et. al. "Structural basis for the activation of FGFR by NCAM". Protein Science 17 (2008) 1698-1705.
McKeehan et al. "The heparan sulfate-fibroblast growth factor family: Diversity of structure and function". Prog. Nucleic Acid Res. Mol. Biol. 59 (1998) 135-176.
Olsen et al. "Insights into the molecular basis for fibroblast growth factor receptor autoinhibition and ligand-binding promiscuity". Proc. Natl. Acad. Sci. USA 101 (2004) 935-940.
Pellegrini et al. "Crystal structure of fibroblast growth factor receptor ectodomain bound to ligand and heparin". Nature 407 (2000) 1029-1034.
Plotnikov et al. "Structural Basis for FGF Receptor Dimerization and Activation". Cell, vol. 98 (1999) 641-650.
Rougon and Hobert. "New insights into the diversity and function of neuronal immunoglobulin superfamily molecules". Annu. Rev. Neurosci. 26 (2003) 207-238.
Soroka et al. "Structure and Interactions of NCAM Ig1-2-3 Suggest a Novel Zipper Mechanism for Homophilic Adhesion". Structure, vol. 10 (2003) 1291-1301.
Walmod et al. "Zippers Make Signals: NCAM-mediated Molecular Interactions and Signal Transduction". Neurochemical Research, vol. 29, No. 11 (2004) pp. 2015-2035.
Wang et al. "Alternately Spliced NH2-terminal Immunoglobulin-like Loop I in the Ectodomain of the Fibroblast Growth Factor (FGF) Receptor 1 Lowers Affinity for Both Heparin and FGF-1". J. Biol. Chem. 270 (1995) 10231-10235.

* cited by examiner

*Primary Examiner* — Cecilia J Tsang
*Assistant Examiner* — Fred Reynolds
(74) *Attorney, Agent, or Firm* — McLane, Graf, Raulerson & Middleton, PA

(57) ABSTRACT

The present invention relates to the use of peptides that are capable of binding to, and modulating the activity of NCAM. The peptides are peptide fragments of FGFRs. They are derived from two distinct binding sites for binding of the immunoglobulin-like module 2 of FGFR to NCAM F3 modules 1-2. The invention further relates to use of said peptides for the production of a medicament for the treatment of different pathological conditions, wherein NCAM and/or FGFRs play a prominent role.

10 Claims, 6 Drawing Sheets

SEQUENCE LISTING

```
<160> NUMBER OF SEQ ID NOS: 18

<210> SEQ ID NO 1
<211> LENGTH: 10
<212> TYPE: PRT
<213> ORGANISM: Artificial sequence
<220> FEATURE:
<223> OTHER INFORMATION: Derived from FGFR

<400> SEQUENCE: 1

Thr Ser Pro Glu Lys Met Glu Lys Lys Leu
1               5                   10

<210> SEQ ID NO 2
<211> LENGTH: 7
<212> TYPE: PRT
<213> ORGANISM: Artificial sequence
<220> FEATURE:
<223> OTHER INFORMATION: Derived  from FGFR

<400> SEQUENCE: 2

Ala Lys Thr Val Lys Phe Lys
1               5

<210> SEQ ID NO 3
<211> LENGTH: 10
<212> TYPE: PRT
<213> ORGANISM: Artificial sequence
<220> FEATURE:
<223> OTHER INFORMATION: Derived from FGFR

<400> SEQUENCE: 3

Arg Trp Leu Lys Asn Gly Lys Glu Phe Lys
1               5                   10

<210> SEQ ID NO 4
<211> LENGTH: 9
<212> TYPE: PRT
<213> ORGANISM: Artificial sequence
<220> FEATURE:
<223> OTHER INFORMATION: Derived from FGFR

<400> SEQUENCE: 4

Thr Trp Ser Ile Ile Met Asp Ser Val
1               5

<210> SEQ ID NO 5
<211> LENGTH: 12
<212> TYPE: PRT
<213> ORGANISM: Artificial sequence
<220> FEATURE:
<223> OTHER INFORMATION: Derived from FGFR

<400> SEQUENCE: 5

Ser Asp Lys Gly Asn Tyr Thr Cys Ile Val Glu Asn
1               5                   10
```

<210> SEQ ID NO 6
<211> LENGTH: 10
<212> TYPE: PRT
<213> ORGANISM: Artificial sequence
<220> FEATURE:
<223> OTHER INFORMATION: Derived from FGFR

<400> SEQUENCE: 6

Thr Tyr Gln Leu Asp Val Val Glu Arg Ser
1               5                   10

<210> SEQ ID NO 7
<211> LENGTH: 8
<212> TYPE: PRT
<213> ORGANISM: Artificial sequence
<220> FEATURE:
<223> OTHER INFORMATION: fragment of CNTN1
<300> PUBLICATION INFORMATION:
<308> DATABASE ACCESSION NUMBER: SwissProt ID: Q12860

<400> SEQUENCE: 7

Thr Ile Arg Trp Leu Lys Asn Gly
1               5

<210> SEQ ID NO 8
<211> LENGTH: 8
<212> TYPE: PRT
<213> ORGANISM: Artificial sequence
<220> FEATURE:
<223> OTHER INFORMATION: Fragment of pro-neuroregulin
<300> PUBLICATION INFORMATION:
<308> DATABASE ACCESSION NUMBER: SwissProt ID: Q05199

<400> SEQUENCE: 8

Lys Trp Leu Lys Asn Gly Lys Glu
1               5

<210> SEQ ID NO 9
<211> LENGTH: 9
<212> TYPE: PRT
<213> ORGANISM: Artificial sequence
<220> FEATURE:
<223> OTHER INFORMATION: Fragment of neurofascin
<300> PUBLICATION INFORMATION:
<308> DATABASE ACCESSION NUMBER: SwissProt ID: Q9QVN5, O94856

<400> SEQUENCE: 9

Thr Leu Arg Trp Phe Lys Asn Gly Gln
1               5

<210> SEQ ID NO 10
<211> LENGTH: 12
<212> TYPE: PRT
<213> ORGANISM: Artificial sequence
<220> FEATURE:
<223> OTHER INFORMATION: Fragment of nectin-like-2
<300> PUBLICATION INFORMATION:
<308> DATABASE ACCESSION NUMBER: SwissProt ID: Q1WIL9, Q6AYP5

<400> SEQUENCE: 10

Thr Ile Arg Trp Phe Lys Gly Asn Lys Glu Leu Lys
1               5                   10

<210> SEQ ID NO 11
<211> LENGTH: 11
<212> TYPE: PRT
<213> ORGANISM: Artificial sequence
<220> FEATURE:
<223> OTHER INFORMATION: Fragment of nectin-like-3

```
<300> PUBLICATION INFORMATION:
<308> DATABASE ACCESSION NUMBER: SwissProt ID: Q1WIM2

<400> SEQUENCE: 11

Ile Arg Trp Phe Lys Asn Asp Lys Glu Ile Lys
1               5                   10

<210> SEQ ID NO 12
<211> LENGTH: 11
<212> TYPE: PRT
<213> ORGANISM: Artificial sequence
<220> FEATURE:
<223> OTHER INFORMATION: Fragment of L1
<300> PUBLICATION INFORMATION:
<308> DATABASE ACCESSION NUMBER: SwissProt ID: Q9QyQ7

<400> SEQUENCE: 12

Arg Trp Thr Lys Asp Gly Ile His Phe Lys Pro
1               5                   10

<210> SEQ ID NO 13
<211> LENGTH: 13
<212> TYPE: PRT
<213> ORGANISM: Artificial sequence
<220> FEATURE:
<223> OTHER INFORMATION: Fragment of CNTN5
<300> PUBLICATION INFORMATION:
<308> DATABASE ACCESSION NUMBER: SwissProt ID: Q49AF3

<400> SEQUENCE: 13

Thr Tyr Arg Trp Leu Lys Asn Gly Val Pro Leu Ser Pro
1               5                   10

<210> SEQ ID NO 14
<211> LENGTH: 12
<212> TYPE: PRT
<213> ORGANISM: Artificial sequence
<220> FEATURE:
<223> OTHER INFORMATION: fragment of CNTN4
<300> PUBLICATION INFORMATION:
<308> DATABASE ACCESSION NUMBER: SwissProt ID: Q14BL8, Q8IWV2

<400> SEQUENCE: 14

Ser Asp Val Gly Asn Tyr Thr Cys Val Val Thr Asn
1               5                   10

<210> SEQ ID NO 15
<211> LENGTH: 12
<212> TYPE: PRT
<213> ORGANISM: Artificial sequence
<220> FEATURE:
<223> OTHER INFORMATION: Fragment of CNTN6
<300> PUBLICATION INFORMATION:
<308> DATABASE ACCESSION NUMBER: SwissProt ID: P97528

<400> SEQUENCE: 15

Ser Asp Val Gly Asn Tyr Thr Cys Phe Val Thr Asn
1               5                   10

<210> SEQ ID NO 16
<211> LENGTH: 12
<212> TYPE: PRT
<213> ORGANISM: Artificial sequence
<220> FEATURE:
<223> OTHER INFORMATION: Fragment of CNTN2
<300> PUBLICATION INFORMATION:
<308> DATABASE ACCESSION NUMBER: SwissProt ID: Q02246

<400> SEQUENCE: 16
```

```
Ser Asp Glu Gly Lys Tyr Thr Cys Phe Ala Glu Asn
1               5                   10

<210> SEQ ID NO 17
<211> LENGTH: 12
<212> TYPE: PRT
<213> ORGANISM: Artificial sequence
<220> FEATURE:
<223> OTHER INFORMATION: Fragment of CNTN1
<300> PUBLICATION INFORMATION:
<308> DATABASE ACCESSION NUMBER: SwissProt ID: Q12860, Q28106

<400> SEQUENCE: 17

Ser Asp Lys Gly Asn Tyr Ser Cys Phe Val Ser Ser
1               5                   10

<210> SEQ ID NO 18
<211> LENGTH: 12
<212> TYPE: PRT
<213> ORGANISM: Artificial sequence
<220> FEATURE:
<223> OTHER INFORMATION: Fragment of Netrin receptor UNC5D precursor
<300> PUBLICATION INFORMATION:
<308> DATABASE ACCESSION NUMBER: SwissProt ID: Q8K1S2

<400> SEQUENCE: 18

Ser Asp Ser Gly Asn Tyr Thr Cys Met Ala Ala Asn
1               5                   10
```

FIBROBLAST GROWTH FACTOR RECEPTOR-DERIVED PEPTIDES BINDING TO NCAM

FIELD OF INVENTION

The present invention relates to the use of peptides that are capable of binding to, and modulating the activity of NCAM. The peptides are peptide fragments of FGFRs. They are derived from two distinct binding sites for binding of the immunoglobulin-like module 2 of FGFR to NCAM F3 modules 1-2. The invention further relates to use of said peptides for the production of a medicament for the treatment of different pathological conditions, wherein NCAM and/or FGFRs play a prominent role.

BACKGROUND OF INVENTION

Fibroblast growth factor receptors (FGFRs) are a family of four closely related receptor protein tyrosine kinases. Extracellularly they consist of three Ig-like modules and intracellularly of a split tyrosine-kinase module (Powers et al., 2000). The receptors are known as key regulators of morphogenesis, development, angiogenesis, and wound healing.

The fibroblast growth factor receptors (FGFR1-4) can be activated by various fibroblast growth factors (FGF1-23) (McKeehan et al., 1998; Itoh and Ornitz, 2004) and cell adhesion molecules (CAMs) such as the neural cell adhesion molecule (NCAM), CAM L1 and N-cadherin (Doherty and Walsh, 1996; Kiselyov et al., 2003 and 2005). FGFR activation and signaling are dependent on dimerization of the receptor which is induced by a high affinity binding of its ligand, fibroblast growth factor (FGF), and it also requires participation of cell surface heparin or heparan sulphate proteoglycans.

The extracellular part of the prototypical FGFR consists of three Ig modules of the intermediate subtype (Plotnikov et al., 1999; Pellegrini et al., 2000; Kiselyov et al., 2006a). The Ig2 and Ig3 modules mediate binding to FGF and heparin, whereas the Ig1 module has an auto-inhibitory function (Wang et al., 1995; Olsen et al., 2004) by means of a direct binding to Ig2 (Kiselyov et al., 2006b).

NCAM is a cell surface glycoprotein belonging to the Ig superfamily of CAMs (for review see Kiselyov et al., 2005). NCAM can be expressed as three major isoforms (A, B and C) with differences in the cytoplasmic domain. The extracellular part of NCAM is identical for the three isoforms and consists of five Ig-like and two fibronectin type III (F3) modules. NCAM is widely expressed during embryonic development, whereas in the adult organism it is mainly found in tissues of neural origin. NCAM plays a major role during development of the nervous system, mediating adhesion between neural cells and stimulating neurite outgrowth and fasciculation, promoting cell survival and synaptic plasticity (Cremer et al., 1997; Berezin et al., 2000; Bruses and Rutishauser, 2001; Rougon and Hobert, 2003; Walmod et al., 2004). NCAM mediates cell-cell adhesion through homophilic binding and regulates neurite outgrowth via FGFR (Doherty and Walsh, 1996; Kiselyov et al., 2003 and 2005). The FGFR site involved in binding to NCAM has been mapped to the Ig3 module, and the corresponding site in NCAM—to the second F3 module (Kiselyov et al., 2003). The mechanism of the NCAM homophilic binding, although extensively studied, is somewhat controversial, and for a thorough review of the available structural data, see Kiselyov et al., 2005. The Ig1 and Ig2 modules of NCAM were demonstrated by surface plasmon resonance (SPR) to bind to each other, and it was suggested that these modules are involved in a symmetrical double reciprocal interaction (Kiselyov et al., 1997). These data were later confirmed by several research groups using various methods such as nuclear magnetic resonance (NMR) analysis and X-ray crystallography (Jensen et al., 1999; Atkins et al., 1999; Kasper et al., 2000). Recently, the crystal structure of the first three N-terminal modules of NCAM has been determined (Soroka et al., 2003), and based on this structure, a model of the NCAM homophilic binding has been suggested. According to this model, interaction between the Ig1 and Ig2 modules leads to formation of a cis-dimer on the surface of the same cell. The cis-dimers from two opposing cells can be involved in the formation of two kinds of one-dimensional "zippers". When combined, the two "zippers" can form a two-dimensional "zipper".

The different modules of NCAM have been shown to perform distinct functions. Thus, NCAM homophilic binding is believed to depend on the first three Ig modules. The heparin binding sequence is localized to the Ig2 module. FGFR binding has been suggested to reside in the two membrane-proximal F3 modules of NCAM.

The mechanism of FGFR activation by NCAM is not well understood. It is thought that most of the FGFR molecules are involved in a transient interaction with NCAM (Kiselyov et al., 2003). When NCAM is not involved in cell-cell adhesion, the NCAM molecules are supposed to be uniformly spread on the cell surface. However, when NCAM is involved in cell-cell adhesion (via the homophilic binding), NCAM molecules may arrange themselves into the so-called 'zipper'-formations (Soroka et al., 2003), which would lead to clustering of the NCAM molecules and, as a result, to clustering of the FGFR molecules. The increase in the local concentration of the FGFR molecules is expected to increase the number of the FGFR molecules involved in a direct FGFR-FGFR interaction, which would result in the increase of the background FGFR activation (Kiselyov et al., 2005).

It has previously been shown by SPR that the double-module construct of NCAM F3 modules 1-2 binds to the double-module FGFR Ig2-Ig3 construct with a dissociation constant (Kd) of 10 μM (Kiselyov et al., 2003). However, interaction between the individual modules could hardly be detected by SPR. This indicates that both modules of the NCAM and FGFR constructs are involved in the binding, or are necessary for the full-strength binding. Using a more sensitive method (NMR), an interaction between the NCAM F3 module 2 and FGFR Ig3 module has been detected (the binding between the NCAM F3 module 1 and FGFR Ig2 module was not tested). The binding site in the NCAM F3 module 2 was mapped to the FG-loop region of the module, which is located in the module's N-terminus (Kiselyov et al., 2003). This indicates that the C-terminus of the NCAM F3 module 1 together with the N-terminal part of the NCAM F3 module 2 could form a single binding site for FGFR, which may be destroyed when the modules are separated.

SUMMARY OF INVENTION

The present invention describes two novel distinct NCAM binding sites of FGFR Ig2 and discloses the use of peptide sequences derived from said FGFR Ig2 binding sites capable of binding to NCAM and thereby modulating NCAM signalling.

According to the invention a peptide sequence derived from the FGFR Ig2 binding sites which is capable of binding to NCAM comprises about 25 amino acid residues and comprises a fragment of FGFR Ig2.

The use according to the invention relates to induction of differentiation, modulation of proliferation, stimulation of regeneration, neuronal plasticity and survival of cells.

The invention relates to uses of the peptides for the treatment of different pathological conditions, wherein FGFR and/or NCAM plays a role in pathology and/or recovery from disease, for example for a) treatment of conditions of the central and peripheral nervous system associated with postoperative nerve damage, traumatic nerve damage, impaired myelination of nerve fibers, postischaemic damage, e.g. resulting from a stroke, Parkinson's disease, Alzheimer's disease, Huntington's disease, dementias such as multiinfarct dementia, sclerosis, nerve degeneration associated with diabetes mellitus, disorders affecting the circadian clock or neuro-muscular transmission, and schizophrenia, mood disorders, such as manic depression;
b) treatment of diseases or conditions of the muscles including conditions with impaired function of neuro-muscular connections, such as after organ transplantation, or such as genetic or traumatic atrophic muscle disorders; or for treatment of diseases or conditions of various organs, such as degenerative conditions of the gonads, of the pancreas such as diabetes mellitus type I and II, of the kidney such as nephrosis and of the heart, liver and bowel;
c) promotion of wound-healing;
d) prevention of death of heart muscle cells, such as after acute myocardial infarction;
e) promotion of revascularisation;
f) stimulation of the ability to learn and/or the short and/or long-term memory;
g) treatment of cancer.

A) Binding of soluble FGFR Ig2 module to the immobilized NCAM F3 modules.

B) Binding of soluble NCAM F3 modules to the immobilized FGFR Ig2 module. The experiment was repeated 9 times.

Figure 2:
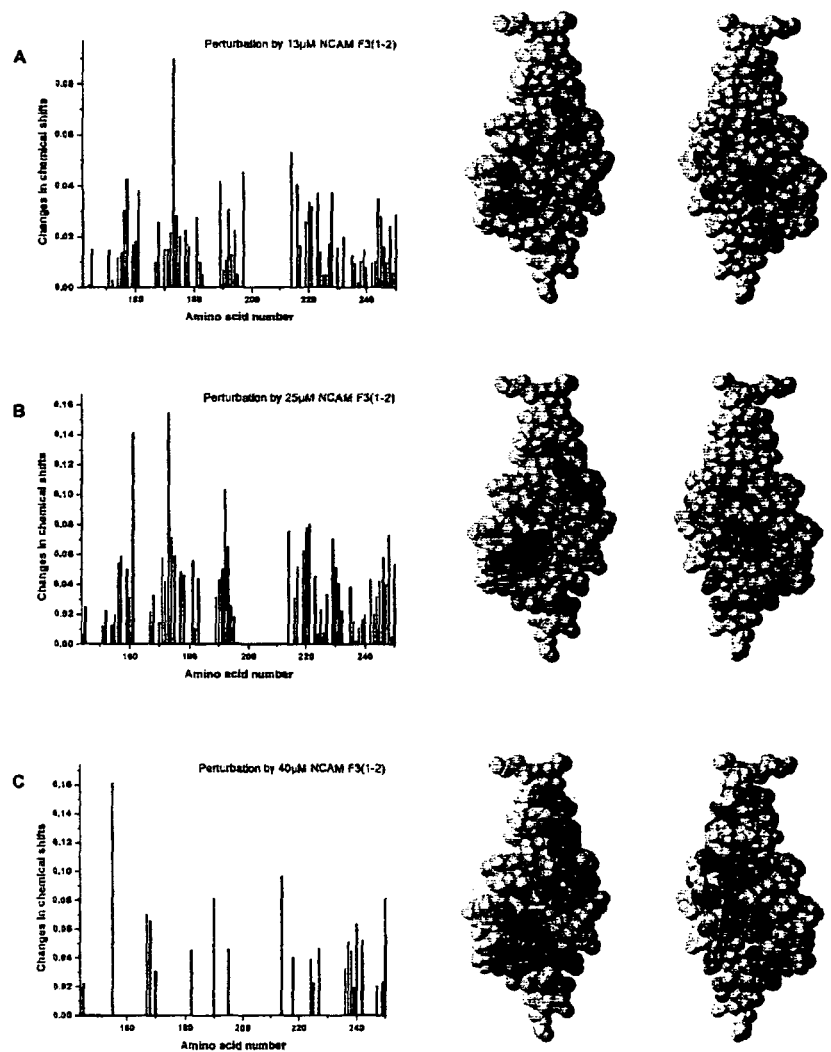

FIG. 2 shows mapping of the Ig2 module's residues involved in binding to NCAM. Changes in chemical shifts of 10 µM $^{15}$N labelled Ig1 module after addition of 13 (A), 25 (B) and 40 (C) µM unlabeled NCAM F3 modules 1-2 and mapping of the significantly perturbed residues onto the structure of the FGFR Ig2 module (right panels). The change of the chemical shift was calculated using the following expression: $((5*\Delta H)^2+(\Delta N)^2)^{0.5}$, where $\Delta H$ is the change of the $^1$H chemical shift and $\Delta N$ is the change of the $^{15}$N chemical shift.

Figure 3:
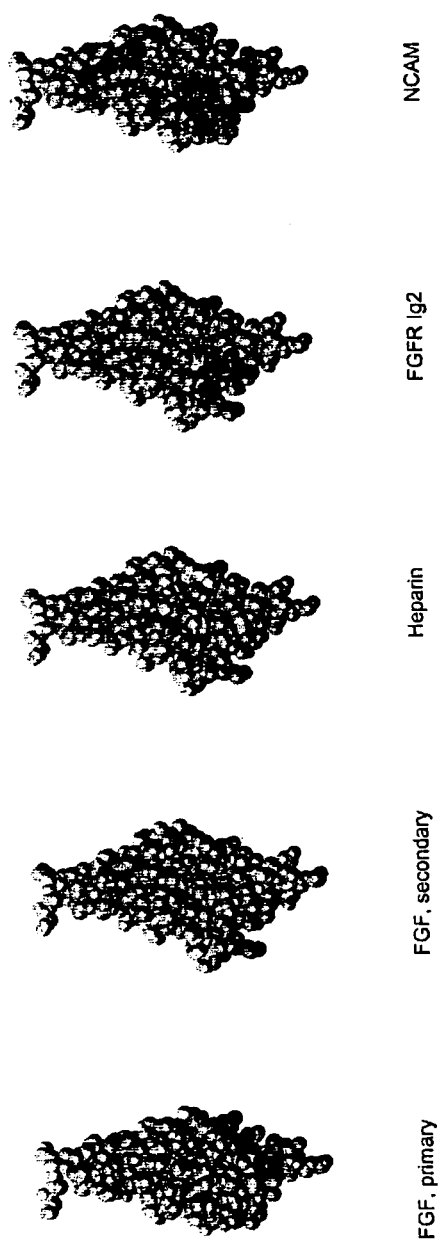

FIG. 3 shows mapping of the various binding sites of the FGFR Ig2 module onto the module's structure.

Figure 4:
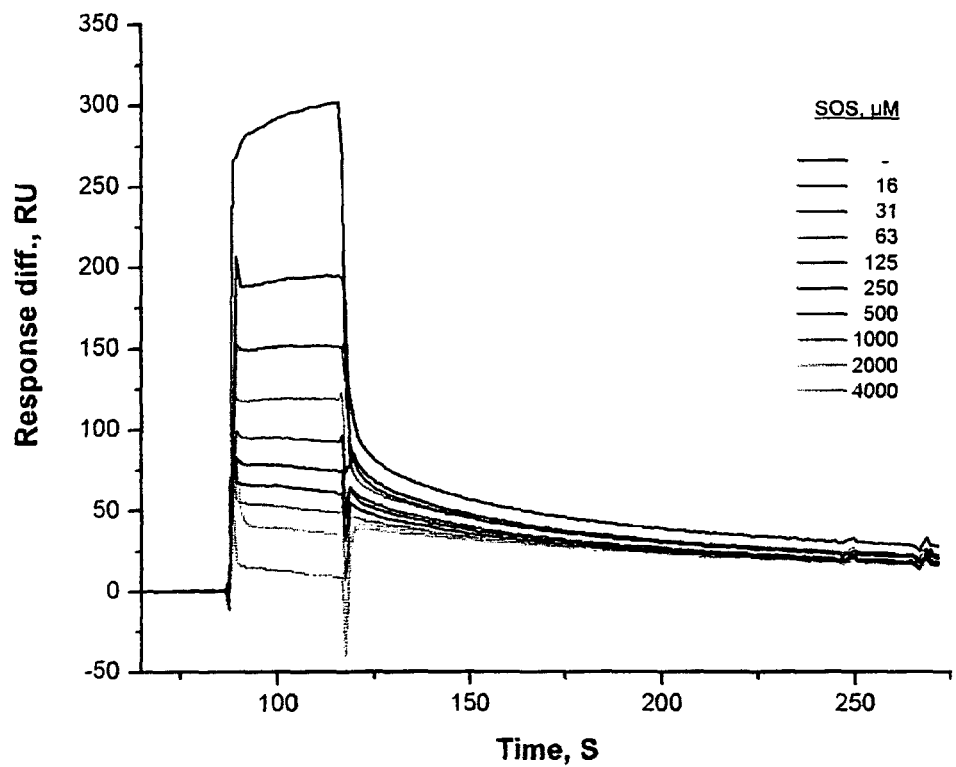

FIG. 4 demonstrates SPR analysis of the inhibitory effect of sucrose octasulphate (SOS) on the FGFR Ig2-NCAM F3(1-2) binding. The binding of 20 µM Ig2 module of FGFR to the immobilized NCAM F3 modules 1-2 was performed using indicated concentrations of SOS. The experiment was repeated 9 times.

Figure 5:
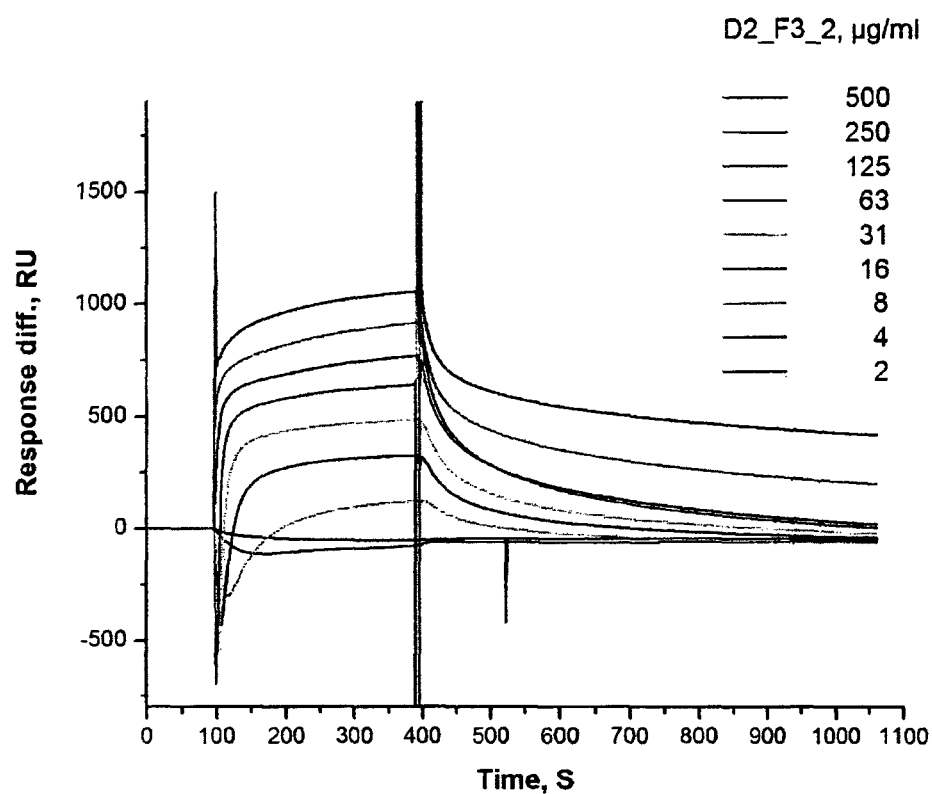

FIG. 5 demonstrates binding of the FGFR1-Ig2 derived peptide AKTVKFK (amino acids 171-177) (SEQ ID NO:2) to the immobilized fibronectin modules (F3(1-2)) of NCAM.

Figure 6:
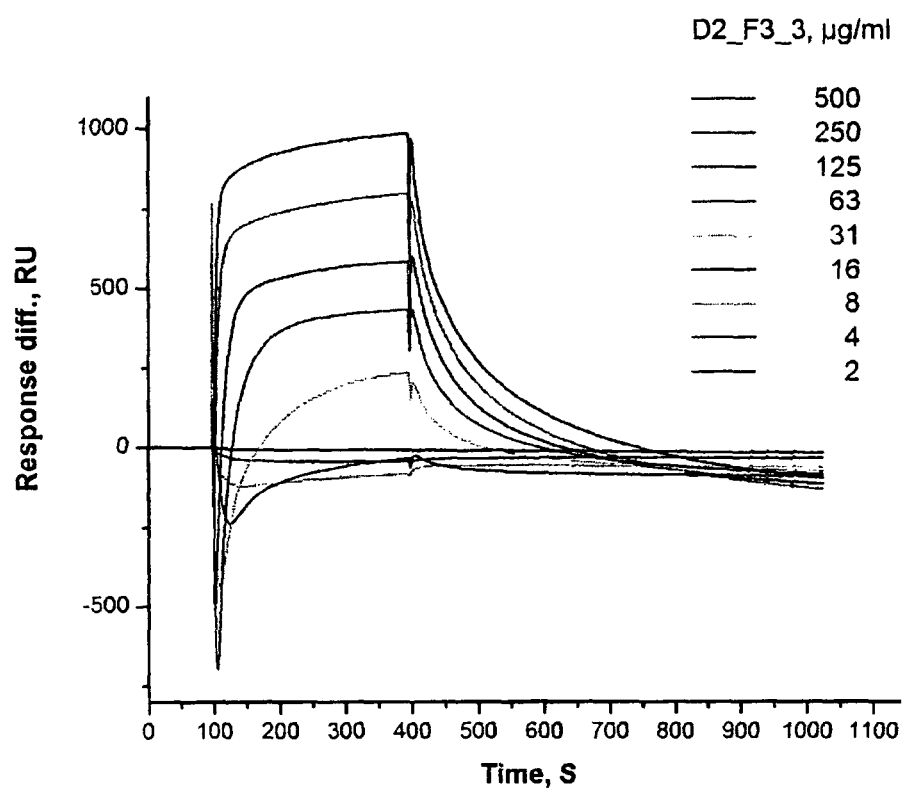

FIG. 6 demonstrates binding of the FGFR1-Ig2 derived peptide RWLKNGKEFK (amino acids 189-198) (SEQ ID NO:3) to the immobilized fibronectin modules (F3(1-2)) of NCAM.

DETAILED DESCRIPTION OF THE INVENTION

A peptide for use according to the invention can be derived from any FGFR, such as FGFR1, FGFR2, FGFR3, FGFR4 and FGFR5 or it may be derived from a variant of any of FGFR1-5, such as a natural or recombinant FGFR variant, for example a FGFR variant produced by alternative splicing, e.g. FGFR1b or FGFR2b, or genetic polymorphism, or any type of recombinant FGFR. It is to be understood that a FGFR of the invention and a variant thereof comprise the NCAM F3 module1-2 binding sites described herein, or comprise at least a part of said binding sites. Examples of FGFRs of the invention which comprise the NCAM F3 module1-2 binding sites of the invention may be the FGFR polypeptides identified in the GenBank database as Ass. Nos: P11362 (corresponding to human FGFR1), P16092 (corresponding to mouse FGFR1), P21802 (corresponding to human FGFR2), P21803 (corresponding to mouse FGFR2) P22607 (corresponding to human FGFR3), Q61861 (corresponding to mouse FGFR3) P22455 (corresponding to human FGFR4), Q03142 (corresponding to mouse FGFR4) or AAK26742 (corresponding to human FGFR5).

The peptide for use according to the invention is a peptide which is capable of modulating activity of NCAM. In one embodiment the peptide may be capable of activating NCAM. In another embodiment, the peptide may be capable of inhibiting NCAM. By the terms "modulation" or "modulating" are meant a change, such as an inhibition or stimulation.

1. Amino Acid Sequence

Peptides for use according to the invention comprise a fragment of FGFR Ig2 which comprises a contiguous amino acid sequence derived from two distinct NCAM F3 module 1-2 binding sites or a fragment, homologue or variant thereof. The first binding site comprises a cluster involving residues $T^{156}$, $S^{157}$, $E^{159}$, $A^{171}$, $T^{173}$, $V^{174}$, $K^{175}$, $S^{181}$, $S^{214}$, $M^{217}$, $D^{218}$, $S^{219}$ and $V^{220}$, from the region a.a 140-251 of FGFR corresponding to FGFR Ig2, and the second binding site comprises a cluster involving residues $M^{161}$, $L^{191}$, $K^{192}$, $N^{193}$, $F^{197}$, $V^{221}$, $T^{229}$, $C^{230}$, $D^{246}$ and $V^{248}$, from the region a.a 140-251 of FGFR corresponding to FGFR Ig2.

In a preferred embodiment the peptides for use according to the invention may comprise a contiguous amino acid sequence which is derived from FGFR Ig2. Accordingly, in this embodiment the amino acid sequence for use according to the invention may be selected from the following amino acid sequences:

TSPEKMEKKL (SEQ ID NO: 1)

AKTVKFK (SEQ ID NO: 2)

RWLKNGKEFK (SEQ ID NO: 3)

TWSIIMDSV (SEQ ID NO: 4)

SDKGNYTCIVEN (SEQ ID NO: 5)

TYQLDVVERS, (SEQ ID NO: 6)

or a fragment, variant or homologue thereof.

In one embodiment a homologue for use according to the invention comprises the motif X1-X2-X3-X4-X5-X6-X7-X8-X9-X10-X11-X12-x13 and fragments or variants thereof, wherein X1 is T or no amino acid,
X3 is a charged amino acid,
X4 is W,
X6 is K,
X5, X7 and X8 are any amino acid,
X2, X9, X10, X11, X12, and X13 are any or no amino acid,
X9 is any or no amino acid,
X10 is any or no amino acid,
X11 is any or no amino acid,
X12 is any or no amino acid,
X13 is any or no amino acid.

Examples of homologues may be:

```
                                           (SEQ ID NO: 7)
TIRWLKNG
(CNTN1, SwissProt ID: Q12860)

(SEQ ID NO: 8)
KWLKNGKE
(pro-neuroregulin, SwissProt ID: Q05199)

(SEQ ID NO: 9)
TLRWFKNGQ
(neurofascin, SwissProt ID: Q9QVN5, O94856)

(SEQ ID NO: 10)
TIRWFKGNKELK
(nectin-like-2, SwissProt ID: Q1WIL9, Q6AYP5)

(SEQ ID NO: 11)
IRWFKNDKEIK
(nectin-like-3, SwissProt ID: Q1WIM2)

(SEQ ID NO: 12)
RWTKDGIHFKP
(L1, SwissProt ID: Q9QyQ7).

(SEQ ID NO: 13)
TYRWLKNGVPLSP
(CNTN5, SwissProt ID: Q49AF3).
```

In another embodiment a homologue for use according to the invention comprises the motif X1-X2-X3-X4-X5-X6-X7-X8-X9-X10-X11-X12 and fragments or variants thereof, wherein
X1 is S,
X2 is D,
X4 is G,
X6 is Y,
X8 is C,
X3, X5, X7, X9, X10, X11, and X12 are any amino acid.

Examples of homologues may be:

```
                                          (SEQ ID NO: 14)
SDVGNYTCVVTN
(CNTN4, SwissProt ID: Q14BL8, Q8IWV2)

(SEQ ID NO: 15)
SDVGNYTCFVTN
(CNTN6, SwissProt ID: P97528)

(SEQ ID NO: 16)
SDEGKYTCFAEN
(CNTN2, SwissProt ID: Q02246)

(SEQ ID NO: 17)
SDKGNYSCFVSS
(CNTN1, SwissProt ID: Q12860, Q28106)

(SEQ ID NO: 18)
SDSGNYTCMAAN
(Netrin receptor UNC5D precursor, SwissProt ID:
Q8K1S2)
```

In the present context the standard one-letter code for amino acid residues as well as the standard three-letter code are applied. Abbreviations for amino acids are in accordance with the recommendations in the IUPAC-IUB Joint Commission on Biochemical Nomenclature Eur. J. Biochem, 1984, vol. 184, pp 9-37. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a peptide for use according to the invention exists as the free carboxylic acid, this may also be specified as "—OH". However, the C-terminal amino acid of a peptide for use according to the invention may be the amidated derivative, which is indicated as "—NH$_2$". Where nothing else is stated the N-terminal amino acid of a polypeptide comprises a free amino-group, this may also be specified as "H—".

A peptide, fragment, homologue or variant for use according to the invention can also comprise one or several unnatural amino acids.

A preferred peptide for use according to the invention is an isolated contiguous peptide sequence which comprises at most 25 amino acid residues. In one embodiment the length of the amino acid sequence of a peptide may be from 3 to 10 amino acid residues, such as for example 4, 5, 6, 7, 8, or 9 amino acid residues. In another embodiment, the length of the amino acid sequence of a peptide may be from 11-25 amino acid residues, such as for example 12, 13, 14, 15, 16, 17, 18, 19, 20, 21, 22, 23 or 24 amino acid residues. The peptides which amino acid sequence has the length in the range of 5 to 15 amino acid residues, such as from 6 to 13, for example 7, 8, 9, 10, 11, or 12, are preferred. It is understood that all peptides for use according to the invention comprise at least one amino acid sequence selected from any of the sequences SEQ ID NOs: 1-6 or a fragment, variant or homologue thereof.

Thus, some embodiments of the invention may relate to the use of a peptide comprising a fragment of a sequence selected from SEQ ID NOs:1-6. Another embodiment may relate to the use of variants of SEQ ID NOs:1-6. A further embodiment may relate to the use of homologues of SEQ ID NOs: 1-6.

For use according to the invention, a variant of an amino acid sequence selected from the sequences SEQ ID NOs: 1-6 may be
 i) an amino acid sequence which has at least 75% identity with a selected sequence, such as 76-80% identity, for example 81-85% identity, such as 86-90% identity, for example 91-95% identity, such as 96-99% identity, wherein the identity is defined as a percentage of identical amino acids in said sequence when it is collated with the selected sequence. The identity between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 9;
 ii) an amino acid sequence which has at least 75% positive amino acid matches with a selected sequence, such as 76-80% positive amino acid matches, for example 81-85% positive amino acid matches, such as 86-90% positive amino acid matches, for example 91-95% positive amino acid matches, such as 96-99% positive amino acid matches, wherein the positive amino acid match is defined as the presence at the same position in two compared sequences of amino acid residues which has similar physical and/or chemical properties. Preferred positive amino acid matches of the present invention are K to R, E to D, L to M, Q to E, I to V, I to L, A to S, Y to W, K to Q, S to T, N to S and Q to R;

iii) an amino acid sequence which is identical to a selected sequence, or it has at least 75% identity with said sequence such as 76-80% identity, for example 81-85% identity, such as 86-90% identity, for example 91-95% identity, such as 96-99% identity, or has at least 75% positive amino acid matches with the selected sequence, such as 76-80% positive amino acid matches, for example 81-85% positive amino acid matches, such as 86-90% positive amino acid matches, for example 91-95% positive amino acid matches, such as 96-99% positive amino acid matches, and comprises other chemical moieties, e.g. phosphoryl, sulphur, acetyl, glycosyl moieties.

The term "variant of a peptide sequence" also means that the peptide sequence may be modified, for example by substitution of one or more of the amino acid residues. Both L-amino acids and D-amino acids may be used. Other modification may comprise derivatives such as esters, sugars, etc., for example methyl and acetyl esters.

In another aspect, variants of the amino acid sequences used according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one asparagine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

It thus follows from the above that the same functional equivalent of a peptide fragment, or fragment of said functional equivalent may comprise more than one conservative amino acid substitution from more than one group of conservative amino acids as defined herein above. The term "conservative amino acid substitution" is used synonymously herein with the term "homologous amino acid substitution".

The groups of conservative amino acids are as the following:

A, G (neutral, weakly hydrophobic),
Q, N, S, T (hydrophilic, non-charged)
E, D (hydrophilic, acidic)
H, K, R (hydrophilic, basic)
L, P, I, V, M, F, Y, W (hydrophobic, aromatic)
C (cross-link forming)

Conservative substitutions may be introduced in any position of a preferred predetermined peptide for use according to the invention or fragment thereof. It may however also be desirable to introduce non-conservative substitutions, particularly, but not limited to, a non-conservative substitution in any one or more positions.

A non-conservative substitution leading to the formation of a functionally equivalent fragment of the peptide for use according to the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like.

Both fragments and variants of amino acid sequences for use according to the invention are the functional equivalents of said sequences.

By the term "functional equivalent" of an amino acid sequence is in the present context meant a molecule which meets the criteria for a variant or a fragment of said amino acid sequence described above and which is capable of one or more functional activities of said sequence or a compound comprising said sequence. In a preferred embodiment the functional equivalent of an amino acid sequence for use according to the invention is capable of binding and modulating activity of NCAM.

The invention relates both to isolated peptides for use according to the invention and fusion proteins comprising peptides for use according to the invention.

In one embodiment, the peptide for use according to the invention is an isolated peptide. By the term "isolated peptide" is meant that the peptide for use according to the invention is an individual compound and not a part of another compound, such as for example a polypeptide comprising more than 25 amino acid residues. The isolated peptide may be produced by use of any recombinant technology methods or chemical synthesis and separated from other compounds, or it may be separated from a longer polypeptide or protein by a method of enzymatic or chemical cleavage and further separated from other protein fragments.

An isolated peptide for use according to the invention may in one embodiment comprise a fragment of FGFR Ig2 which comprises a contiguous amino acid sequence derived from two distinct NCAM F3 module 1-2 binding sites. The peptide with Seq ID NO:1 contains three a.a from the first binding site and one a.a. from the second binding site. The peptide with Seq ID NO:2 contains four a.a. from the first binding site. The peptide with Seq. ID NO:3 contains four a.a from the second binding site. The peptide with Seq ID NO:4 contains four a.a from the first binding site. The peptide with Seq ID NO:5 contains two a.a. from the second binding site. The peptide with Seq ID NO:6 contains two a.a from the second binding site. An isolated peptide for use according to the invention may in one embodiment comprise a fragment of FGFR Ig2 which comprises a contiguous amino acid sequence derived from two distinct NCAM F3 module 1-2 binding sites, selected from SEQ ID NOs:1-6 or a fragment or homologue thereof. In another embodiment the isolated peptide may consist of one or more of the sequences SEQ ID Nos:1-6.

Production of Peptide Sequences

The peptide sequences of the present invention may be prepared by any conventional synthetic methods, recombinant DNA technologies, enzymatic cleavage of full-length proteins which the peptide sequences are derived from, or a combination of said methods.

Recombinant Preparation

Thus, in one embodiment the peptides of the invention are produced by use of recombinant DNA technologies.

The DNA sequence encoding a peptide or the corresponding full-length protein the peptide originates from may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein of peptide origin, using DNAase I according to a standard protocol (Sambrook et al., Molecular cloning: A Laboratory manual. 2 rd ed., CSHL Press, Cold Spring Harbor, N.Y., 1989). The present invention relates to full-length proteins selected from the groups of proteins identified above. The DNA encoding the full-length proteins of the invention may alternatively be fragmented using specific restriction endonucleases. The fragments of DNA are further purified using standard procedures described in Sambrook et al., Molecular cloning: A Laboratory manual. 2 rd ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a full-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell Biol. 1:854-864), the MT-1 (metallothionein gene) promoter (Palmiter et al., 1983, Science 222: 809-814) or the adenovirus 2 major late promoter. A suitable promoter for use in insect cells is the polyhedrin promoter (Vasuvedan et al., 1992, FEBS Lett. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al, eds., Plenum Press, New York), or the TPI1 (U.S. Pat. No. 4,599,311) or ADH2-4-c (Russell et al., 1983, Nature 304: 652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op.cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-5-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet. 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Synthetic Preparation

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteins. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the peptide sequences of the invention are produced synthetically, in particular, by the Sequence Assisted Peptide Synthesis (SAPS) method.

Peptides may be synthesised either batchwise in a polyethylene vessel equipped with a polypropylene filter for filtration or in the continuous-flow version of the polyamide solid-phase method (Dryland, A. and Sheppard, R. C., (1986) J. Chem. Soc. Perkin Trans. I, 125-137.) on a fully automated peptide synthesiser using 9-fluorenylmethyloxycarbonyl (Fmoc) or tert.-Butyloxycarbonyl, (Boc) as N-a-amino protecting group and suitable common protection groups for side-chain functionality's.

Medicament

It is an objective of the invention to provide a compound capable of modulating the activity of NCAM, said compound being concerned by the invention as a medicament for the treatment of diseases, wherein modulation of NCAM signalling may be considered as an essential condition for curing.

Accordingly, the invention relates to the use of one or more of the peptides comprising a sequence corresponding to a Ig2 NCAM binding site of the FGF receptor or a fragment thereof or a variant for the manufacture of a medicament.

In one embodiment the medicament of the invention comprises at least one of the amino acid sequences set forth in SEQ ID NOS: 1-6 or fragments or variants or homologues of said sequences, or fragments or variants of said homologues. In another embodiment the medicament of the invention comprises an antibody capable of binding to an epitope comprising a binding site of the invention or a fragment or variant of said antibody.

The medicament may in one aspect prevent death of cells in vitro or in vivo, wherein the composition is administered to a subject, in vitro or in vivo in an effective amount of one or more of the compounds described above or a composition as described below, so as to prevent cell death of NCAM presenting cells in several tissues and organs as discussed herein.

The medicament of the invention comprises an effective amount of one or more of the compounds as defined above, or a composition comprising compound as defined above, in combination with pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the peptides of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred μg active ingredient per administration with a preferred range of from about 0.1 μg to 5000 μg per kilo body weight. Using monomeric forms of the compounds, the suitable dosages are often in the range of from 0.1 μg to 5000 μg per kilo body weight, such as in the range of from about 0.1 μg to 3000 μg per kilo body weight, and especially in the range of from about 0.1 μg to 1000 μg per kilo body weight. Using multimeric forms of the compounds, the suitable dosages are often in the range of from 0.1 μg to 1000 μg per kilo body weight, such as in the range of from about 0.1 μg to 750 μg per kilo body weight, and especially in the range of from about 0.1 μg to 500 μg per kilo body weight such as in the range of from about 0.1 μg to 250 μg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For most indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promote delivery of the active substance to its target.

In many instances, it will be necessary to administrate the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

As discussed above, the present invention relates to treatment of individuals for inducing differentiation, modulating proliferation, stimulate regeneration, neuronal plasticity and survival of NCAM presenting cells in vitro or in vivo, the treatment involving administering an effective amount of one or more compounds as defined above.

Another strategy for administration is to implant or inject cells capable of expressing and secreting the compound in question. Thereby the compound may be produced at the location where it is going to act.

Treatment

Treatment according to the invention is in one embodiment useful for inducing differentiation, modulating proliferation, stimulating regeneration, neuronal plasticity and survival of cells, for example cells being implanted or transplanted.

In further embodiment the treatment may be for stimulation of survival of cells which are at risk of dying due to a variety of factors, such as traumas and injuries, acute diseases, chronic diseases and/or disorders, in particular degenerative diseases normally leading to cell death, other external factors, such as medical and/or surgical treatments and/or diagnostic methods that may cause formation of free radicals or otherwise have cytotoxic effects, such as X-rays and chemotherapy. In relation to chemotherapy the NCAM binding peptides used according to the invention are useful in cancer treatment.

Thus, the treatment comprises treatment and/or prophylaxis of cell death in relation to diseases or conditions of the central and peripheral nervous system, such as postoperative nerve damage, traumatic nerve damage, e.g. resulting from spinal cord injury, impaired myelination of nerve fibers, postischaemic damage, e.g. resulting from a stroke, multiinfarct dementia, multiple sclerosis, nerve degeneration associated with diabetes mellitus, neuro-muscular degeneration, schizophrenia, Alzheimer's disease, Parkinson's disease, or Huntington's disease.

Also, in relation to diseases or conditions of the muscles including conditions with impaired function of neuro-muscular connections, such as genetic or traumatic atrophic muscle disorders; or for the treatment of diseases or conditions of various organs, such as degenerative conditions of the gonads, of the pancreas, such as diabetes mellitus type I and II, of the kidney, such as nephrosis the compounds according to the invention may be used for inducing differentiation, modulating proliferation, stimulate regeneration, neuronal plasticity and survival, i.e. stimulating survival.

Furthermore, the treatment may be for preventing cell death of heart muscle cells, such as after acute myocardial infarction, in order to induce angiogenesis. Furthermore, in one embodiment the treatment is for the stimulation of the survival of heart muscle cells, such as survival after acute myocardial infarction. In another aspect the treatment is for revascularisation, such as after injuries.

It is also within the scope of the invention a use of the peptides for the promotion of wound-healing. The present peptides are capable of stimulating angiogenesis and thereby they can promote the wound healing process.

The invention further discloses a use of peptides in the treatment of cancer. Regulation of activation of NCAM is important for tumor agiogenesis, proliferation and spreading.

In yet a further embodiment a use of the peptides is for the stimulation of the ability to learn and/or of the short and/or long term memory, as NCAM activity is important for differentiation of neural cells.

In still another embodiment a peptide for use according to the invention is for the treatment of body damages due to alcohol consumption. Developmental malformations of foetuses, long-term neurobehavioral alterations, alcoholic liver disease are particularly concerned.

Therapeutic treatment of prion diseases including using a peptide is still another embodiment of the invention.

In particular the use according to the invention of a peptide may be for the treatment of clinical conditions, such as neoplasms such as malignant neoplasms, benign neoplasms, carcinoma in situ and neoplasms of uncertain behavior, cancer in breast, thyroidal, pancreas, brain, lung, kidney, prostate, liver, heart, skin, blood organ, muscles (sarcoma), cancers with dysfunction and/or over- or under-expression of specific receptors and/or expression of mutated receptors or associated with soluble receptors, such as but not limited to Erb-receptors and FGF-receptors, diseases of endocrine glands, such as diabetes mellitus I and II, pituitary gland tumor, psychoses, such as senile and presenile organic psychotic conditions, alcoholic psychoses, drug psychoses, transient organic psychotic conditions, Alzheimer's disease, cerebral lipidoses, epilepsy, general paresis [syphilis], hepatolenticular degeneration, Huntington's chorea, Jakob-Creutzfeldt disease, multiple sclerosis, Pick's disease of the brain, polyarereiti nodosa, syphilis, schizophrenic disorders, affective psychoses, neurotic disorders, personality disorders, including character neurosis, nonpsychotic personality disorder associated with organic brain syndromes, paranoid personality disorder, fanatic personality, paranoid personality (disorder), paranoid traits, sexual deviations and disorders or dysfunctions (including reduced sexual drive for what ever reason), mental retardation, disease in the nervesystem and sense organs, such as affecting sight, hearing, smell, feeling, tasting, cognitive anomalies after disease, injury (e.g. after trauma, surgical procedure, and violence), inflammatory disease of the central nervous system, such as meningitis, encephalitis, cerebral degenerations such as Alzheimer's disease, Pick's disease, senile degeneration of brain, senility NOS, communicating hydrocephalus, obstructive hydrocephalus, Parkinson's disease including other extra pyramidal disease and abnormal movement disorders, spinocerebellar disease, cerebellar ataxia, Marie's Sanger-Brown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, syringomyelia and syringobulbia, vascular myelopathies, acute infarction of spinal cord (embolic) (nonembolic), arterial thrombosis of spinal cord, edema of spinal cord, hematomyelia, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [Riley-Day syndrome], idiopathic peripheral autonomic neuropathy, carotid sinus syncope or syndrome, cervical sympathetic dystrophy or paralysis. peripheral autonomic neuropathy in disorders classified elsewhere, amyloidosis, diseases of the peripheral nerve system, brachial plexus lesions, cervical rib syndrome, costoclavicular syndrome, scalenus anticus syndrome, thoracic outlet syndrome, brachial neuritis or radiculitis NOS, including in newborn. Inflammatory and toxic neuropathy, including acute infective polyneuritis, Guillain-Barre syndrome, Postinfectious polyneuritis, polyneuropathy in collagen vascular disease, disorders of the globe including disorders affecting multiple structures of eye, such as purulent endophthalmitis, diseases of the ear and mastoid process, chronic rheumatic heart disease, ischaemic heart disease, arrhythmia, diseases in the pulmonary system, respiratory system, sensoring e.g. oxygene, astma, abnormality of organs and soft tissues in newborn, including in the nerve system, complications of the administration of anesthetic or other sedation in labor and delivery, diseases in the skin including infection, insufficient circulation problem, burn injury and other mechanic and/or physical injuries, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chiasm, injury to optic pathways, injury to visual cortex, unspecified blindness, injury to other cranial nerve(s), injury to other and unspecified nerves, poisoning by drugs, medicinal and biological substances, genetic or traumatic atrophic muscle disorders; or for the treatment of diseases or conditions of various organs, such as degenerative conditions of the gonads, of the pancreas, such as diabetes mellitus type I and II, of the kidney, such as nephrosis. Scrapie, Creutzfeldt-Jakob disease, Gerstmann-Straussler-Sheinker (GSS) disease; pain syndrome, encephalitis, drug/alcohol abuse, anxiety, postoperative nerve damage, peri-operative ischemia, inflammatory disorders with tissue damage, either by affecting the infections agent or protecting the tissue, HIV, hepatitis, and following symptoms, autoimmune disorders, such as rheumatoid arthritis, SLE, ALS, and MS. Anti-inflammatory effects, asthma and other allergic reactions, acute myocardial infarction, and other related disorders or sequel from AMI, metabolic disorders, such as obscenity lipid disorders (e.g. hyper cholestorolamia, artheslerosis, disorders of amino-acid transport and metabolism, disorders of purine and pyrimidine metabolism and gout, bone disorders, such as fracture, osteoporosis, osteo arthritis (OA), Atrophic dermatitis, psoriasis, infection cased disorders, stem cell protection or maturation in vivo or in vitro.

Peptides used according to the invention may also be used for the prevention and treatment of achondroplasia, hypochondroplasia, platyspondylic lethal skeletal dysplasia, thanatophoric dysplasia, Antley-Bixler syndrome, Apert syndrome, Beare-Stevenson syndrome, Crouzon syndrome, Jackson-Weiss syndrome, Pfeiffer syndrome, and Saethre-Chotzen syndrome.

Antibody

It is an objective of the present invention to provide the use of an antibody, antigen binding fragment or recombinant protein thereof capable of selectively binding to an epitope comprising a contiguous amino acid sequence derived from two distinct FGFR Ig2-NCAM F3 module 1-2 binding sites or a fragment, homologue or variant thereof. The peptide with Seq ID NO:1 contains three a.a from the first binding site and one a.a. from the second binding site. The peptide with Seq ID NO:2 contains four a.a. from the first binding site. The peptide with Seq. ID NO:3 contains four a.a from the second binding site. The peptide with Seq ID NO:4 contains four a.a from the first binding site. The peptide with Seq ID NO:5 contains two a.a. from the second binding site. The peptide with Seq ID NO:6 contains two a.a from the second binding site. The invention relates to any antibody capable of selectively binding to an epitope comprising a contiguous amino acid sequence derived from two distinct FGFR Ig2-NCAM F3 module 1-2 binding sites, selected from any of the sequences set forth in SEQ ID NOS: 1-6, or a fragment or variant of said sequence.

By the term "epitope" is meant the specific group of atoms (on an antigen molecule) that is recognized by (that antigen's) antibodies. The term "epitope" is the equivalent to the term "antigenic determinant". The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Novotny J, & Haber E. Proc Natl Acad Sci U S A. 82(14):4592-6, 1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ) based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In the context of both the therapeutic and screening methods described below, preferred embodiments are the use of an antibody or fragment thereof that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

The term "antibody fragment" is used herein interchangeably with the term "antigen binding fragment".

Antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it is has similar or immunological properties relative to antibody that binds with specificity to an epitope comprising a peptide sequence selected from any of the sequences identified herein as SEQ ID NOs: 1-6, or a fragment of said sequences. Thus, in context of the present invention the term "antibody fragment" is identical to term "antigen binding fragment".

Antibody fragments retain some ability to selectively bind with its antigen or receptor. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction.

(4) F(ab')$_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, NY, 1994.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

The invention also contemplates multivalent antibodies having at least two binding domains. The binding domains may have specificity for the same ligand or for different ligands. In one embodiment the multispecific molecule is a bispecific antibody (BsAb), which carries at least two different binding domains, at least one of which is of antibody origin. Multivalent antibodies may be produced by a number of methods. Various methods for preparing bi- or multivalent antibodies are for example described in U.S. Pat. Nos. 5,260, 203; 5,455,030; 4,881,175; 5,132,405; 5,091,513; 5,476,786; 5,013,653; 5,258,498; and 5,482,858.

The invention contemplate both polyclonal and monoclonal antibody, antigen binding fragments and recombinant proteins thereof which are capable of binding an epitope according to the invention.

The preparation of polyclonal antibodies is well-known to those skilled in the art. See, for example, Green et al. 1992. Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1, which are hereby incorporated by reference.

The preparation of monoclonal antibodies likewise is conventional. See, for example, Kohler & Milstein, Nature, 256: 495-7 (1975); Coligan, et al., sections 2.5.1-2.6.7; and Harlow, et al., in: Antibodies: A Laboratory Manual, page 726, Cold Spring Harbor Pub. (1988), Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG). In: Methods in Molecular Biology, 1992, 10:79-104, Humana Press, NY.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., 1984, Proc Natl Acad Sci 81: 6851-6855.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in $E.$ $coli$ of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as $E.$ $coli$. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', $F(ab')_2$ or other antigen-binding subsequences of antibodies) that contain a minimal sequence derived from non-human immunoglobulin, such as the eitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising an epitope(s) described herein, is one of the preferred embodiments of the invention.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., 1986, Nature 321, 522-525; Reichmann et al., 1988, Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

The generation of antibodies may be achieved by any standard methods in the art for producing polyclonal and monoclonal antibodies using natural or recombinant fragments of a sequence selected from any of the sequences identified as SEQ ID NOs: 1-6, as an antigen. Such antibodies may be also generated using variants or fragments of SEQ ID NOs: 1-6.

The antibodies may also be produced in vivo by the individual to be treated, for example, by administering an immunogenic fragment according to the invention to said individual. Accordingly, the present invention further relates to a vaccine comprising an immunogenic fragment described above.

The application also relates to a method for producing an antibody of the invention said method comprising a step of providing of an immunogenic fragment described above.

The invention relates both to an antibody, which is capable of modulating, such as enhancing or attenuating, biological function of NCAM in particular a function related to neural cell growth and survival, and to an antibody, which can recognise and specifically bind to NCAM without modulating biological activity thereof.

The invention relates to use of the above antibodies for therapeutic applications involving the modulation of activity of NCAM In one aspect the invention relates to the use of a pharmaceutical composition comprising an antibody described above.

EXAMPLES

1. Binding between FGFR Ig2 and NCAM F3 Module 1-2

Methods

To study the binding properties between the FGFR Ig2 module and NCAM, we used recombinant proteins of the NCAM F3 modules 1-2 and the FGFR1 Ig2 module. Both proteins were properly folded as judged by one-dimensional NMR.

Production of Recombinant Proteins

The Ig2 module of mouse FGFR1 (IIIc isoform) and rat NCAM F3 modules 1-2 were produced. Both proteins were expressed in a KM71 strain of yeast expression system of *P. pastoris* (Invitrogen, USA). The FGFR Ig module 2 consists of AGHHHHHH and amino acids 140-251 of FGFR (SwissProt p16092) and the combined F3 modules 1 and 2 consist of AGHHHHHH and amino acids 507-611 and 507-705 of NCAM (SwissProt p13596), respectively. For the protein expression the following media were used: BMGH (0.1 M potassium phosphate pH 6.0, 3.4 g/L yeast nitrogen base (without amino acids and ammonium sulphate), 10 g/L ammonium sulphate, 400 µg/L D-biotin, 60 mg/L L-histidine, 2% glycerol) and BMMH (0.1 M potassium phosphate pH 6.0, 3.4 g/L yeast nitrogen base (without amino acids and ammonium sulphate), 10 g/L ammonium sulphate, 400 µg/L D-biotin, 60 mg/L L-histidine, 1% methanol). For production of the $^{15}$N labelled protein, $^{15}$N labelled ammonium sulphate was used in the media in the following concentrations: 3.5 g/L in BMGH and 1.5 g/L in BMMH. All the proteins were purified by affinity chromatography using Ni$^{2+}$-NTA resin (Qiagen) and/or ion exchange chromatography and gel filtration.

NMR Analysis

The following samples were used recording of NMR spectra: 10 µM $^{15}$N FGFR Ig2 module with or without 13, 25, 40 µM NCAM F3 modules 1-2. The buffer was 10 mM sodium phosphate containing 150 mM NaCl, pH 7.4. The samples were analyzed by recording a $^{15}$N-Heteronuclear single quantum correlation (HSQC) spectra using the standard set-up provided by Protein Pack. HSQC spectrum of a $^{15}$N-labeled protein records the one-bond coupling of an H—N bond and is therefore a useful tool for monitoring site-specific perturbations. The chemical shift changes of the signals provide a means to identify the amino acid residues whose NMR signals are perturbed by the binding of another molecule. The addition of F3 NCAM modules led to either line-broadening, chemical shift changes or, for certain residues, disappearance of the NMR signals. The residues with NMR signal undergoing significant chemical shift changes (greater than 0.03 ppm for the 13 µM F3 module and 0.05 ppm for the 25 and 40 µM F3 modules) or disappearing completely were considered to be specifically perturbed by the binding. The spectra were processed by NMRPipe (Delaglio et al., 1995) and analysed by Pronto3D (Kjaar et al., 1994). The NMR experiments were performed using Varian Unity Inova 750 and 800 MHz spectrometers. All spectra were recorded at 298 K.

SPR Analysis

Immobilization of the NCAM and FGFR modules and binding analysis were performed using a BIAcore2000 instrument (Biosensor AB, Sweden) at 25° C. using 10 mM sodium phosphate containing 150 mM NaCl (pH 7.4) as running buffer. Data were analyzed by nonlinear curve fitting using the manufacturer's software. The FGFR Ig module 2 and NCAM F3 modules 1-2 were immobilized on sensor chip CM5 using an amine coupling kit (Biosensor AB) as follows: the chip was activated by 20 µl activation solution; the protein was immobilized using 12 µl of 20 µg/ml protein in 10 mM sodium acetate buffer (pH 6.0); the chip was blocked by 35 µl blocking solution. The curves corresponding to the difference between binding to ligand (immobilized molecule) and a blank chip were used for analysis.

Results and Discussion

Binding of FGFR Ig2 to NCAM

It has previously been shown by SPR that the double-module construct of NCAM F3 modules 1-2 binds to the double-module FGFR Ig2-Ig3 construct with a dissociation constant (Kd) of 10 µM (Kiselyov et al., 2003). However, interaction between the individual modules could hardly be detected by SPR. This indicates that both modules of the NCAM and FGFR constructs are involved in the binding, or are necessary for the full-strength binding. Using a more sensitive method (NMR), an interaction between the NCAM F3 module 2 and FGFR Ig3 module has been detected (the binding between the NCAM F3 module 1 and FGFR Ig2 module was not tested). The binding site in the NCAM F3 module 2 was mapped to the FG-loop region of the module, which is located in the module's N-terminus (Kiselyov et al., 2003). This indicates that the C-terminus of the NCAM F3 module 1 together with the N-terminal part of the NCAM F3 module 2 could form a single binding site for FGFR, which may be destroyed when the modules are separated.

Figure 1:
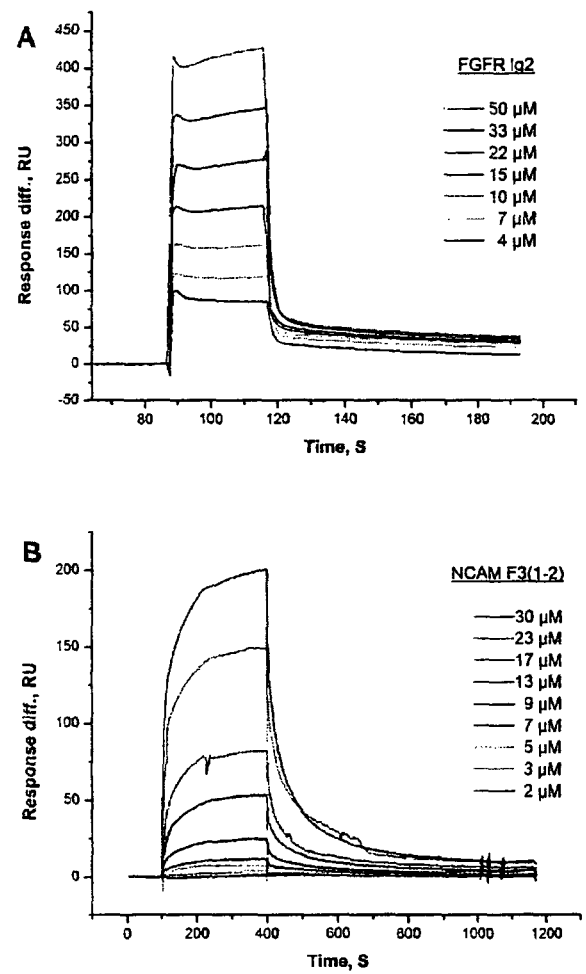
FIG. 1 shows SPR analysis of the binding between the FGFR Ig2 module and NCAM F3 modules 1-2.

Binding of the FGFR Ig2 module to the combined NCAM F3 modules 1-2 was tested. Using SPR, binding of soluble Ig2 to immobilized NCAM F3 modules 1-2 was detected with an estimated KD value of 35 µM (see FIG. 1A). When the Ig2 module was immobilized, the KD value for the binding of soluble F3 modules 1-2 was estimated to be 12 µM (FIG. 1B). These data show that the Ig2 module of FGFR is also involved in binding to NCAM F3 modules.

Identification of the FGFR Ig2 Residues Involved in Binding to NCAM

Since the Ig2 module of FGFR binds to NCAM F3 modules 1-2, it was of interest to determine the residues of the Ig2 module involved in this binding. For this purpose, we used NMR analysis. In a $^{15}$N-HSQC spectrum of a $^{15}$N-labeled protein, a signal for all amino acids with both a nitrogen and a proton can be observed. The changes in chemical shifts of the signals provide a method for identification in a protein of amino acid residues that are perturbed by the binding of another molecule. The specter of 10 µM Ig2 module was recorded in the presence of 0, 13, 25 or 40 µM F3 modules 1-2. Addition of the NCAM F3 modules led to broadening of the resonance lines, changes of the chemical shifts and disappearance of the NMR signals for some of the residues. The residues with significant changes of the chemical shifts (greater than 0.03 ppm for 13 µM and 0.05 ppm for 25 and 40 µM F3 modules) or with the completely disappeared NMR signals were considered to be significantly perturbed by the binding. The recorded changes of chemical shifts and mapping of the significantly perturbed residues onto the structure of the Ig2 module (Plotnikov et al., 1999) are shown in FIG. 2. As can be seen from FIG. 2C, addition of 40 µM F3 modules perturbed most of the Ig2 module's residues and most of these residues are those with the disappeared signals. This indicates that the exchange between the bound and non-bound form of the Ig2 module is intermediate on the NMR time-scale. Addition of 13 µM F3 modules led to perturbation of few residues (FIG. 2A), while 25 µM F3 modules perturbed 28 residues which form two clusters on the opposite 'sides' of the module (FIG. 2B). The first binding site comprises a cluster involving residues $T^{156}$, $S^{157}$, $E^{159}$, $A^{171}$, $T^{173}$, $V^{174}$, $K^{175}$, $S^{181}$, $S^{214}$, $M^{217}$, $D^{218}$, $S^{219}$ and $V^{220}$, from the region a.a 140-251 of FGFR corresponding to FGFR Ig2, and the second binding site comprises a cluster involving residues $M^{161}$, $L^{191}$, $K^{192}$, $N^{193}$, $F^{197}$, $V^{221}$, $T^{229}$, $C^{230}$, $D^{246}$ and $V^{248}$, from the region a.a 140-251 of FGFR corresponding to FGFR Ig2. Perturbation of these residues demonstrates that the presence of the NCAM F3 modules close to the FGFR Ig2 module alters the chemical environment at the perturbed residues, indicating that the perturbed residues are either a part or in the vicinity of the binding site for the interaction between NCAM and FGFR.

One of the identified clusters (the first one) is located in the close vicinity of the sites in Ig2 for binding of FGF, heparin and Ig2 (FIG. 3) (Plotnikov et al., 1999; Pellegrini et al., 2000). As can be seen from FIG. 3, heparin is expected to inhibit binding of the Ig2 module to NCAM. To verify this assumption, we tested sucrose octasulphate (SOS), a well-known heparin analogue, for its ability to inhibit binding of soluble Ig2 to the immobilized NCAM F3 modules. As appears from FIG. 4, SOS was indeed capable of inhibiting the Ig2-NCAM binding, as expected given that the first cluster is located close to the heparin-binding site of the Ig2 module.

We suggest that in the absence of NCAM mediated cell-cell adhesion, that is when NCAM is not involved in the homophilic binding, the FGFR molecules do not bind substantially to NCAM. However, when NCAM is involved in homophilic binding, the NCAM molecules become clustered due to formation of zipper-like structures. This would allow an FGFR molecule to bind simultaneously to two neighbouring NCAM molecules with a much higher affinity than to the individual NCAM molecules, which is supposed to ensure an efficient NCAM-FGFR interaction. Thus FGFR is expected to bind to and become activated by NCAM only when NCAM is clustered through a homophilic binding mechanism.

REFERENCES

Atkins A R, Osborne M J, Lashuel H A, Edelman G M, Wright P E, Cunningham B A, Dyson H J (1999). Association between the first two immunoglobulin-like domains of the neural cell adhesion molecule N-CAM. *FEBS Lett.* 451: 162-168.

Berezin V, Bock E and Poulsen F M (2000). The neural cell adhesion molecule. *Current Opinion in Drug Discovery&Development* 3:605-609.

Bruses J L, Rutishauser U (2001). Roles, regulation, and mechanism of polysialic acid function during neural development. *Biochemie* 83:635-643.

Cremer H, Chazal G, Goridis C, Represa A (1997). NCAM is essential for axonal growth and fasciculation in the hippocampus. *Mol Cell Neurosci.* 8:323-335.

Delaglio F, Grzesiek S, Vuister G W, Zhu G, Pfeifer J and Bax A (1995). NMRPipe: a multidimensional spectral processing system based on UNIX pipes. *J Biomol NMR* 6:277-293.

Doherty P and Walsh F S (1996). CAM-FGF Receptor Interactions: A Model for Axonal Growth. *Mol Cell Neurosci.* 8:99-111.

Itoh N and Ornitz D M (2004). Evolution of the Fgf and Fgfr gene families. *Trends Genet.* 20:563-569.

Jensen P H, Soroka V, Thomsen N K, Ralets I, Berezin V, Bock E, Poulsen F M (1999). Structure and interactions of NCAM modules 1 and 2, basic elements in neural cell adhesion. *Nat Struct Biol.* 6:486-493.

Kasper C, Rasmussen H, Kastrup J S, Ikemizu S, Jones E Y, Berezin V, Bock E, Larsen I K (2000). Structural basis of cell-cell adhesion by NCAM. *Nat Struct Biol.* 7:389-393.

Kiselyov V V, Berezin V, Maar T E, Soroka V, Edvardsen K, Schousboe A, Bock E (1997). The first immunoglobulin-like neural cell adhesion molecule (NCAM) domain is involved in double-reciprocal interaction with the second immunoglobulin-like NCAM domain and in heparin binding. *J Biol. Chem.* 272:10125-10134.

Kiselyov V V, Kochoyan A, Poulsen F M, Bock E, Berezin V (2006b). Elucidation of the mechanism of the regulatory function of the Ig1 module of the fibroblast growth factor receptor 1. *Protein Sci.* 15:2318-2322.

Kiselyov V V, Bock E, Berezin V, Poulsen F M (2005). Structural biology of NCAM homophilic binding and activation of FGFR. *J. Neurochem.* 94:1169-1179.

Kiselyov V V, Bock E, Berezin V, Poulsen F M (2006a). NMR Structure of the First Ig Module of mouse FGFR1. *Protein Sci.* 15:1512-1515.

Kiselyov V V, Skladchikova G, Hinsby A M, Jensen P H, Kulahin N, Soroka V, Pedersen N, Tsetlin V, Poulsen F M, Berezin V and Bock E (2003). Structural basis for a direct interaction between FGFR1 and NCAM and evidence for a regulatory role of ATP. *Structure* 11:691-701.

Kjaar M, Andersen K V and Poulsen F M (1994). *Meth Enzymol.* 239:288-307.

McKeehan W L, Wang F, Kan M (1998). The heparin sulphate-fibroblast growth factor family: diversity of structure and function. *Prog Nucleic Acid Res Mol Biol* 59:135-176.

Olsen S K, Ibrahimi O A, Raucci A, Zhang F, Eliseenkova A V, Yayon A, Basilico C, Linhardt R J, Schlessinger J and Mohammadi M (2004). Insights into the molecular basis for fibroblast growth factor receptor autoinhibition and ligand-binding promiscuity. *Proc Natl Acad Sci USA* 101: 935-940.

Pellegrini L, Burke D F, von Delft F, Mulloy B and Blundell T L (2000). Crystal structure of fibroblast growth factor receptor ectodomain bound to ligand and heparin. *Nature* 407:1029-1034.

Plotnikov A N, Schlessinger J, Hubbard S R and Mohammadi M (1999). Structural basis for FGF receptor dimerization and activation. *Cell* 98:641-650.

Rougon G, Hobert O (2003). New insights into the diversity and function of neuronal immunoglobulin superfamily molecules. *Annu Rev Neurosci.* 26:207-238.

Soroka V, Kolkova K, Kastrup J S, Diederichs K, Breed J, Kiselyov V V, Poulsen F M, Larsen I K, Welte W, Berezin V, Bock E, Kasper C (2003). Structure and interactions of NCAM Ig1-2-3 suggest a novel zipper mechanism for homophilic adhesion. *Structure* 11:1291-1301.

Walmod P S, Kolkova K, Berezin V, Bock E (2004). Zippers make signals: NCAM-mediated molecular interactions and signal transduction. *Neurochem Res.* 29:2015-2035.

Wang F, Kan M, Yan G, Xu J and McKeehan W L (1995). Alternately spliced NH2-terminal immunoglobulin-like Loop I in the ectodomain of the fibroblast growth factor (FGF) receptor 1 lowers affinity for both heparin and FGF-1. *J Biol. Chem.* 270:10231-10235.

---

The invention claimed is:

1. A method for modulating NCAM signalling comprising administering to a subject in need thereof an isolated peptide consisting of an amino acid sequence derived from FGFR Ig2 and selected from the group consisting of:

AKTVKFK (SEQ ID NO: 2)
and
RWLKNGKEFK (SEQ ID NO: 3)

or a variant thereof having one conservative amino acid substitution, wherein said peptide specifically binds to NCAM.

2. The method according to claim 1, wherein said peptide is in monomeric form or multimeric form.

3. The method according to claim 1, wherein the peptide specifically binds to the NCAM fibronectin 3, module 1 or 2.

4. The method according to claim 1, wherein said peptide activates NCAM signaling.

5. The method according to claim 1, wherein said peptide induces neurite outgrowth and/or promotes neural cell survival and/or stimulates learning and/or memory.

6. The method according to claim 1 wherein the subject has multi-infarct dementia, multiple sclerosis, or Alzheimer's disease.

7. The method according to claim 1 wherein said administering stimulates the ability to learn and/or of the short and/or long term memory in the subject.

8. The method according to claim 1, wherein said peptide consists of the amino acid sequence of SEQ ID NO:2.

9. The method according to claim 1, wherein said peptide consists of the amino acid sequence of SEQ ID NO:3.

10. The method according to claim 1, wherein said peptide is in multimeric form.

* * * * *